(12) United States Patent
Fattman

(10) Patent No.: US 6,825,246 B1
(45) Date of Patent: *Nov. 30, 2004

(54) HYDROCOLLOID ADHESIVE COMPOSITIONS

(75) Inventor: George Fattman, Mt. Laurel, NJ (US)

(73) Assignee: Bristol-Myers Squibb Company, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/433,161

(22) Filed: Nov. 3, 1999

Related U.S. Application Data

(60) Provisional application No. 60/106,799, filed on Nov. 3, 1998.

(51) Int. Cl.[7] .............................................. C08L 15/00
(52) U.S. Cl. ......................... 523/111; 524/37; 524/35; 524/55; 524/57; 524/58; 524/247; 524/474
(58) Field of Search .......................... 523/111; 524/271, 524/274, 474, 55, 56, 57, 58, 35, 37, 22

(56) References Cited

U.S. PATENT DOCUMENTS

| | | | | |
|---|---|---|---|---|
| 4,231,369 A | * | 11/1980 | Sorensen et al. | 128/283 |
| 4,294,936 A | * | 10/1981 | Korpman | 525/93 |
| 4,789,699 A | * | 12/1988 | Kieffer et al. | 524/271 |
| 5,169,706 A | * | 12/1992 | Collier, IV et al. | 428/152 |
| 6,120,899 A | * | 9/2000 | Cameron et al. | 428/407 |

FOREIGN PATENT DOCUMENTS

EP  0756854 A1  2/1997

\* cited by examiner

*Primary Examiner*—Katarzyna Wyrozebski
(74) *Attorney, Agent, or Firm*—Stuart E. Krieger

(57) ABSTRACT

The present invention is directed to pressure sensitive hydrocolloid adhesive compositions having probe tack of about 300–750 grams force, tensile strength of about 500–3500 grams/cm$^2$ and saline absorbency of about 500–5000 grams/m$^2$/24 hours.

23 Claims, No Drawings

HYDROCOLLOID ADHESIVE COMPOSITIONS

This Appln claims benefit of Provisional No. 60/106,799 filed Nov. 3, 1998.

BACKGROUND OF THE INVENTION

The present invention relates to pressure sensitive adhesive compositions and more particularly to pressure sensitive hydrocolloid adhesive compositions suited for use in ostomy, wound and incontinence care.

The compositions of this invention can be used for example to hold ostomy or incontinence devices onto the body of the user or to hold wound dressings in position for treating skin ailments or as the wound dressing itself.

Various hydrocolloid adhesive compositions suitable for medical uses are disclosed in the patent literature, e.g., U.S. Pat. No. 3,339,549 (Chen); U.S. Pat. No. 4,192,785 (Chen, et al.); U.S. Pat. No. 4,166,051 (Cilento, et al.); U.S. Pat. No. 4,393,080 (Pawelchak, et al.); U.S. Pat. No. 3,612,053 (Pratt, et al.); U.S. Pat. No. 4,231,369 (Sorensen, et al.); U.S. Pat. No. 3,908,658 (Marsan); U.S. Pat. No. 4,367,732 (Poulsen, et al.); U.S. Pat. No. 4,378,018 (Alexander, et al.); and U.S. Pat. No. 4,393,150 (Krones).

Hydrocolloid adhesives are composed of powdered hydrocolloids dispersed in an elastomeric polymer matrix. They have been found to make excellent pressure sensitive adhesives for attachment of devices to the skin. Useful hydrocolloid adhesives depend on their initial tack, cohesive strength, and absorbency to achieve wearing times on skin of up to 10 days or longer. It is also required that components of hydrocolloid adhesives be cost effective, easy to process, and compatible with other device components.

OBJECT OF THE INVENTION

It is an object of the present invention to provide a biocompatible hydrocolloid adhesive composition simultaneously having preferred probe tack, tensile strength and saline absorbency as provided in Table I.

TABLE 1

| Characteristic | Usefulness Range | Preferred Range | |
|---|---|---|---|
| Probe Tack | About 300–750 grams, force | About 500–650 grams, force | |
| Tensile Strength | About 500–3500 grams/cm$^2$ | About 1500–2500 g/cm$^2$ extruded | About 500–1500 non-extruded |
| Saline Absorbency | About 500–5000 g/m$^2$/day | About 2000–3500 g/m$^2$/d extruded | About 1500–2500 non-extruded |

It is also an object of the present invention to provide a biocompatible adhesive that is easy to process, cost efficient, durable and that doesn't swell excessively when hydrated.

It is an object to achieve with the present invention probe tack values above about 300 grams, force, as this value has been found to be desirable for attaining a strong initial bond to the skin. Improved bonds are generally obtained with increased tack, though too strong a bond may damage skin upon removal.

It is also an objective of the present invention to achieve acceptable shear-strength and peel properties. It has been determined that tensile strengths of about 500–3500 g/square centimeter are desirable. It is also recognized, however, that decreased flexibility or reduced adhesion may result if cohesive strength is excessive.

DESCRIPTION OF THE INVENTION

The adhesive compositions of the present invention utilize a poly(ethylene-propylene) rubber (EPR) having a broad molecular weight, amorphous structure and an ethylene content of 50% or less. The EPR is also a random copolymer and easy to process. The preferred EPR is Vistalon 404, Exxon Chemical Co. Low molecular weight species in the EPR favor bond formation while higher molecular weight species enhance cohesive and peel strength. A compatible tackifying resin for this elastomer preferred for optimum tackification is a low molecular weight, highly hydrogenated polyvinylcyclohexane. Commercially available examples are Regalrez® 1085 or Regalrez® 1094. (Hercules, Inc.). It is further preferred that the polyvinylcyclohexane have a softening point below body temperature and most preferably below room temperature such that it may further improve the wetting of skin by the elastomeric component. A commercially available example is Regalrez® 1018 (Hercules, Inc.). In particular, the use of low softening point resin allows for increasing the concentration of tackifier by a corresponding reduction in the concentration of plasticizing components. Both factors favorably influence adhesion, while retaining flexibility that may be lost when resins of higher softening point are employed. Adhesion is easily measured by using a task test to determine the bond forming capability.

Because hydrocolloid adhesives are composed of an elastomeric phase and a hydrocolloid phase, proper optimization of the adhesive formulation requires simultaneous optimization of the individual phases. While some interaction does occur between phases, the elastomeric phase is primarily responsible for the adhesive and cohesive strength properties, and the hydrocolloid phase is primarily responsible for the overall moisture handling and moisture interaction characteristics of the formulation. Adhesion and cohesion typically represent a balance of competing behaviors, and strong elastomers may not yield very effective adhesives. Moisture handling is more than just absorption, per se, but must be thought of in terms of absorption rate, absorption capacity, and the properties of the hydrated material. The hydrocolloid phase is key in determining these characteristics.

The ability of the adhesive to form a bond to the skin is directly related to the probe tack of the adhesive. Tack is generated by the action of tackifying resins to enhance wetting of the skin by the elastomeric components of the formulation. Modification of elastomers by tackifiers enables elastomers to form bonds while retaining their cohesiveness and contribute strength to the overall formulation. Compatibility of the tackifier with the elastomer is believed to be a key factor in tackifier effectiveness, as is the presence of low molecular weight species in the elastomer. Typically, the elastomer is blended with a styrenic block copolymer for optimum cohesive strength.

In order to attain adhesion to the skin for more than 1 or 2 days, it is necessary that the adhesive absorb fluid at a rate greater than or equal to the rate of transepidermal water loss (TEWL), approximately 7–10 g/square meter per hour on average. The actual absorption rate required to maintain skin adhesion can in practice be somewhat greater than this value as a function of weather, physical activity, etc. To obtain the minimum absorption capacity, this absorption rate should be multiplied over the wearing time.

Absorption by the adhesive is necessary to effectively manage perspiration from the skin. Without this capability, the adhesive would fail after short wearing times, and skin condition would be adversely affected. However, absorption also causes degradation of the adhesive component resulting from hydration and chemical attack by stomal discharge. This degradation occurs because the absorbent hydrocolloids act regardless of the source of the fluid absorbed, either perspiration or stoma effluent. Therefore, limiting absorption to the minimum necessary to manage perspiration will limit how stoma fluid will impact dressing integrity.

Denture adhesives are an example of water activated adhesives. Typically, sodium carboxy-methyl cellulose (NaCMC) is used as a component of these formulations. A blend of NaCMC grades is used to achieve desired properties. Differences between grades are defined by the degree of substitution (DS) of carboxymethyl groups onto the anhydroglucose repeat units of the cellulose chain. Higher DS grades (>1.0) are used to impart a high rate of absorption, while lower to moderate DS grades (<1.0) are included for their long term cohesiveness. One further requirement of the formulation is that its response to moisture must not compromise the performance of the device for which the adhesive was intended. As hydrocolloid adhesives absorb moisture they begin to swell. The hydrating hydrocolloid powders transform the rubbery elastomer phase into a more gelatinous composition that appears to grow. Typically this growth occurs in the direction of a free surface. For wound dressings the growth is into the wound. For ostomy skin barriers the growth is toward the stoma, and is called turtlenecking for its resemblance to the collar on a turtleneck sweater.

In some cases turtlenecking is desirable, as it has been reported to provide an effective seal around the stoma itself and prevents leakage of stomal effluent and undermining of the skin barrier. However, excessive amounts of turtlenecking can have the opposite effect, causing effluent to be diverted from the pouch and against the skin. Excessive turtlenecking in hydrocolloid adhesives can be avoided by limiting elongation of the elastomeric phase during hydration. Key factors in attaining acceptable turtlenecking are the choice of elastomer, the balance of absorption rate and capacity within the limits described above, the balance of cohesive and adhesive properties in the elastomer phase.

In contrast to denture adhesives, it has been discovered that use of higher DS CMC grades in combination with low to moderate DS grades reduces the rate of moisture absorption in hydrocolloid adhesives. In other words, as the average degree of substitution of the CMC in the formulation increases, the absorption rate of the hydrocolloid adhesive decreases. Further, overall absorption capacity increases. As a result, longer wearing times are possible because the influence of stomal effluent on adhesive integrity is reduced, though the film forming and water activated bonding capabilities of CMC are retained. Additionally, turtlenecking characteristics are favorably impacted.

Although it is possible to lower the absorption rate of the formulation by using different hydrocolloids having a weaker affinity for water, the impact on overall adhesive properties is not as favorable as with the use of higher DS CMC. Examples 34 and 35 below show how use of pregelatinized starch, a low absorbing hydrocolloid, reduces the absorption rate of the formulation. However, in contrast with the performance of high DS CMC, the overall absorption capacity of the adhesive is not increased. Further, the water activated bonding power of hydrated starch to human skin is not believed to be as effective as either pectin or especially CMC. Therefore, addition of a minor amount of starch, or other low absorbing hydrocolloids, may expand the useful range of this invention to the extent that the effectiveness of the preferred hydrocolloids in extending wear time is not compromised.

Addition of a small amount of a powdered cellulose, which is not a hydrocolloid but a water swellable powder, is also useful for reducing moisture absorption while still being of similar composition to NaCMC. A further benefit of adding powdered cellulose is that it improves cohesive strength of the overall formulation.

As a result of the fact that the EPR is can be readily blended with the other formulation components, a variety of conventional compounding processes are believed to be suitable for obtaining a homogeneous mixture. Potential mixing processes would include solvent blending, continuous or semi-continuous compounding, calendering or milling, and internal or external mixers. The preferred mixing process utilizes a high intensity batch mixer, which has been heated to between 250 and 330° F. The process proceeds by alternating additions of rubber or block copolymer with any of the powders and one of the low molecular weight components, which are mixed in groups until homogeneous. The entire process proceeds for as long as about 90 minutes or more. The low molecular weight components include any of the tackifiers and the plasticizer. The plasticizer used should be a low molecular weight polymer appropriately chosen to reduce the modulus of the formulation, promote flexibility and conformability of the adhesive, and be suitable for contact with the skin or mucosal tissue. Preferably petrolatum may be used.

Formulated adhesive mass may then be formed by any of various means into smooth sheets. The preferred forming methods are extrusion or compression. A useful thickness range for the adhesive is believed to be in the range between 0.005 inch and 0.25 inch. This adhesive sheet may be laminated with a wide variety of films, foams, non-woven or other fabrics, etc. and also to paper, some of which may have been coated with release agents to promote removal. The adhesive sheet may be cut into useful sizes, shapes and dimensions including discs, profiles, contours or other constructions of adhesive articles. Laminates may be added readily to the adhesive when it is maintained at elevated temperature. Preferred methods of lamination include a roll based lamination station or a compression type process. Cutting may be accomplished using several methods, the preferred ones being a rotary cutting die or a platen type cutting die.

EXAMPLES

Table 2 provides a listing of 25 hydrocolloid adhesives pursuant to the present invention. Each of these compositions are blended to produce compositions with the characteristics listed in Table 2A within the usefulness ranges of Table 1.

Additional examples showing the utility of the invention are shown in Table 6.

Examples of the trade names for components of the compositions are the following:

ethylene propylene rubber—Vistalon 404, Exxon Chemical Co.;

styrenic block copolymer—Kraton D1107, Shell Chemical Co.;

tackifier (solid)— Piccotac 95, Hercules, Inc.;

tackifier (liquid)— Regalrez 1018, Hercules, Inc.;

NaCMC—Sodium Carboxymethyle cellulose FCC grade with

DS7=degree of substitution=0.7

DS12=degree of substitution=1.2 pectin—Pectin, USP 100;

powdered cellulose, FCC—Solka Floc 200 FCC, Fiber Sales & Development Corp.

Antioxidant—Irganox 1010, Ciba Geigy Corp.;
Plasticizer—white petrolatum, USP;
Cyclo-aliphatic tackifying resin—Relarez 1094, Hercules, Inc.;
Hydrogenated rosin ester—Pentalyn H., Hercules, Inc.;
Pregelatinized starch—Prejel PA5, Avebe, Inc.

Examples 1–4 and 17–20 of Tables 2 and 2A demonstrate acceptable performance within the usefulness ranges of Table 1. These examples represent a base adhesive which has no liquid tackifier, high DS DMC, or powdered cellulose but still achieves useful properties. Improvements to probe tack resulting from the use of low softening point tackifier are shown in Table 3. The effectiveness of high degree of substitution sodium carboxymethyl cellulose to reduce absorption is shown in Table 5. The ability of powdered cellulose to reduce absorption and increase strength is demonstrated in Table 4.

Measurements of probe tack were based on the method described in ASTM D2979 using an inverted probe machine. In this test, conducted at room temperature, the dwell time was 1 second, and the approach speed was 1 cm/second. Tensile measurements were based on ASTM test method D412 with the crosshead speed set to 200 mm/minute using a dumb bell shaped test specimen. The peak tensile strength is reported. Absorbency measurements were conducted based on the British Pharmacopoeia method wherein a flat adhesive specimen of known weight and area is exposed to 0.9% saline solution. The exposed adhesive is incubated at body temperature for 24 hours and re-weighed. The weight difference per area is reported.

TABLE 2A

| Example | Probe Tack g tack force | Tensile Strength g/cm$^2$ (non-extruded) | 24 Hr Saline Absorption g/sq.m/24 hr (non-extruded) |
|---|---|---|---|
| 1 | 432 | 852 | 1937 |
| 2 | 411 | 2966 | 3459 |
| 3 | 470 | 860 | 1439 |
| 4 | 418 | 1465 | 2936 |
| 5 | 559 | 1690 | 2111 |
| 6 | 481 | 1451 | 2479 |
| 7 | 517 | 1637 | 2947 |
| 8 | 615 | 1690 | 3507 |
| 9 | 586 | 1587 | 2859 |
| 10 | 418 | 1574 | 2113 |
| 11 | 438 | 2065 | 1538 |
| 12 | 477 | 1757 | 2257 |
| 13 | 572 | 1032 | 3590 |
| 14 | 449 | 1919 | 3237 |
| 15 | 425 | 1830 | 2446 |
| 16 | 599 | 1312 | 1869 |
| 17 | 508 | 662 | 2200 |
| 18 | 426 | 1538 | 2705 |
| 19 | 529 | 824 | 3249 |
| 20 | 491 | 1205 | 2209 |
| 21 | 531 | 998 | 2843 |
| 22 | 420 | 2183 | 2861 |
| 23 | 394 | 587 | 2326 |
| 24 | 450 | 632 | 3107 |
| 25 | 597 | 873 | 2426 |

TABLE 2

| Example | Ethylene-Propylene Rubber | Styrenic Block Copolymer | Tackifying Resin | Anti-oxidant | NaCMC DS7 | Pectin | Low Softening Point Tackifier | Plasticizer | NaCMC DS12 | Powdered Cellulose |
|---|---|---|---|---|---|---|---|---|---|---|
| 1 | 6.0% | 13.0% | 28.0% | 0.5% | 33.0% | 10.0% | | 9.5% | | |
| 2 | 2.0% | 10.0% | 33.0% | 0.5% | 27.0% | 20.0% | | 7.5% | | |
| 3 | 10.0% | 16.0% | 24.0% | 0.5% | 32.5% | 5.0% | | 12.0% | | |
| 4 | 7.0% | 10.5% | 28.0% | 0.5% | 26.0% | 20.0% | | 8.0% | | |
| 5 | 6.0% | 13.0% | 30.0% | 0.5% | 35.0% | 7.0% | | 8.5% | | |
| 6 | 6.0% | 13.0% | 28.0% | 0.5% | 35.0% | 7.0% | 2.0% | 8.5% | | |
| 7 | 6.0% | 13.0% | 25.0% | 0.5% | 35.0% | 7.0% | 5.0% | 8.5% | | |
| 8 | 6.0% | 13.0% | 28.0% | 0.5% | 35.0% | 7.0% | 5.0% | 5.5% | | |
| 9 | 6.0% | 13.0% | 28.0% | 0.5% | 30.0% | 7.0% | 5.0% | 5.5% | 5.0% | |
| 10 | 6.0% | 13.0% | 28.0% | 0.5% | 20.0% | 7.0% | 5.5% | 5.5% | 15.0% | |
| 11 | 6.0% | 13.0% | 28.0% | 0.5% | 10.0% | 7.0% | 5.5% | 5.5% | 25.0% | |
| 12 | 6.0% | 13.0% | 25.0% | 0.5% | 15.0% | 15.0% | 5.5% | 5.0% | 15.0% | |
| 13 | 5.0% | 12.5% | 25.0% | 0.5% | 28.0% | 15.0% | 2.0% | 7.0% | 5.0% | |
| 14 | 5.0% | 12.5% | 25.0% | 0.5% | 25.0% | 15.0% | 2.0% | 7.0% | 5.0% | 3.0% |
| 15 | 5.0% | 12.5% | 25.0% | 0.5% | 22.0% | 15.0% | 2.0% | 7.0% | 5.0% | 6.0% |
| 16 | 5.0% | 12.5% | 28.0% | 0.5% | 20.0% | 15.0% | 2.0% | 7.0% | 8.0% | 2.0% |
| 17 | 5.0% | 12.5% | 28.0% | 0.5% | 30.0% | 15.0% | | 9.0% | | |
| 18 | 2.0% | 15.5% | 28.0% | 0.5% | 30.0% | 15.0% | | 9.0% | | |
| 19 | 8.0% | 9.5% | 28.0% | 0.5% | 30.0% | 15.0% | | 9.0% | | |
| 20 | 5.0% | 12.5% | 28.0% | 0.5% | 30.0% | 15.0% | | 9.0% | | |
| 21 | 5.0% | 12.5% | 28.0% | 0.5% | 30.0% | 15.0% | 3.0% | 6.0% | | |
| 22 | 2.0% | 15.5% | 28.0% | 0.5% | 30.0% | 15.0% | 6.0% | 3.0% | | |
| 23 | 8.0% | 9.5% | 25.0% | 0.5% | 30.0% | 15.0% | 3.0% | 9.0% | | |
| 24 | 8.0% | 9.5% | 25.0% | 0.5% | 30.0% | 15.0% | 6.0% | 6.0% | | |
| 25 | 8.0% | 9.5% | 28.0% | 0.5% | 20.0% | 15.0% | 3.0% | 6.0% | 10.0% | |

TABLE 3

Examples Showing Improvement in Tack Using Low Softening Point Tackifier

| Example | Ethylene-Propylene Rubber % w/w | Styrenic Block Copolymer % w/w | Tackifying Resin % w/w | Anti-oxidant % w/w | NaCMC Low DS % w/w | Pectin % w/w | Low Softening Point Tackifier % w/w | Plasticizer % w/w | NaCMC High DS % w/w | Powdered Cellulose % w/w | Probe Tack g task force |
|---|---|---|---|---|---|---|---|---|---|---|---|
| 1 | 6.0% | 13.0% | 28.0% | 0.5% | 33.0% | 10.0% | | 9.5% | | | 432 |
| 2 | 2.0% | 10.0% | 33.0% | 0.5% | 27.0% | 20.0% | | 7.5% | | | 411 |
| 3 | 10.0% | 16.0% | 24.0% | 0.5% | 32.5% | 5.0% | | 12.0% | | | 470 |
| 4 | 7.0% | 10.5% | 28.0% | 0.5% | 26.0% | 20.0% | | 8.0% | | | 418 |
| 6 | 6.0% | 13.0% | 28.0% | 0.5% | 35.0% | 7.0% | 2.0% | 8.5% | | | 481 |
| 7 | 6.0% | 13.0% | 25.0% | 0.5% | 35.0% | 7.0% | 5.0% | 8.5% | | | 517 |
| 8 | 6.0% | 13.0% | 28.0% | 0.5% | 35.0% | 7.0% | 5.0% | 5.5% | | | 615 |
| 21 | 5.0% | 12.5% | 28.0% | 0.5% | 30.0% | 15.0% | 3.0% | 6.0% | | | 531 |
| 25 | 8.0% | 9.5% | 28.0% | 0.5% | 20.0% | 15.0% | 3.0% | 6.0% | | 10.0% | 597 |

TABLE 4

Examples Showing Improvement in Tensile Strength Using Powdered Cellulose

| Example | Ethylene-Propylene Rubber % w/w | Styrenic Block Copolymer % w/w | Tackifying Resin % w/w | Anti-oxidant % w/w | NaCMC Low DS % w/w | Pectin % w/w | Low Softening Point Tackifier % w/w | Plasticizer % w/w | NaCMC High DS % w/w | Powdered Cellulose % w/w | Tensile Strength g/cm$^2$ |
|---|---|---|---|---|---|---|---|---|---|---|---|
| 13 | 5.0% | 12.5% | 25.0% | 0.5% | 28.0% | 15.0% | 2.0% | 7.0% | 5.0% | | 1032 |
| 14 | 5.0% | 12.5% | 25.0% | 0.5% | 25.0% | 15.0% | 2.0% | 7.0% | 5.0% | 3.0% | 1919 |
| 15 | 5.0% | 12.5% | 25.0% | 0.5% | 22.0% | 15.0% | 2.0% | 7.0% | 5.0% | 6.0% | 1830 |
| 16 | 5.0% | 12.5% | 28.0% | 0.5% | 20.0% | 15.0% | 2.0% | 7.0% | 8.0% | 2.0% | 1312 |

TABLE 5

Examples Showing Reduced Absorption Using High Degree of Substitution CMC

| Example | Ethylene-Propylene Rubber % w/w | Styrenic Block Copolymer % w/w | Tackifying Resin % w/w | Anti-oxidant % w/w | NaCMC Low DS % w/w | Pectin % w/w | Low Softening Point Tackifier % w/w | Plasticizer % w/w | NaCMC High DS % w/w | Powdered Cellulose % w/w | 24 Hr Saline Absorption g/sq · m/24 hr |
|---|---|---|---|---|---|---|---|---|---|---|---|
| 8 | 6.0% | 13.0% | 28.0% | 0.5% | 35.0% | 7.0% | 5.0% | 5.5% | | | 3507 |
| 9 | 6.0% | 13.0% | 28.0% | 0.5% | 30.0% | 7.0% | 5.0% | 5.5% | 5.0% | | 2859 |
| 10 | 6.0% | 13.0% | 28.0% | 0.5% | 20.0% | 7.0% | 5.5% | 5.5% | 15.0% | | 2113 |
| 11 | 6.0% | 13.0% | 28.0% | 0.5% | 10.0% | 7.0% | 5.5% | 5.5% | 25.0% | | 1538 |
| 12 | 6.0% | 13.0% | 25.0% | 0.5% | 15.0% | 15.0% | 5.5% | 5.0% | 15.0% | | 2257 |
| 25 | 8.0% | 9.5% | 28.0% | 0.5% | 20.0% | 15.0% | 3.0% | 6.0% | 10.0% | | 2426 |

TABLE 6

Additional Formulation Examples Demonstrating the Utility of the Invention

| Example | Ethylene Propylene Rubber | Styrenic Block Copolymer | Tackifying Resin | Anti-oxidant | NaCMC DS7 | Pectin | Low Softening Point Tackifier | Plasticizer | NaCMC DS12 | Powdered Cellulose | Hydrogenated Rosin Ester | Cyclo-aliphatic tackifying Resin |
|---|---|---|---|---|---|---|---|---|---|---|---|---|
| 26 | 20 | 2 | 25 | 0.5 | 14 | 14 | 5.5 | 5 | 14 | | | |
| 27 | 5 | 10 | 30.5 | 0.5 | 15.5 | 30.5 | | 8 | | | | |
| 28 | 5 | 10 | 25 | 0.5 | 33 | 17 | | 9.5 | | | | |
| 29 | 5 | 10 | 25 | 0.5 | 35 | 12.5 | | 12 | | | | |
| 30 | 5 | 12.5 | | 0.5 | 20 | 15 | 2 | 7 | 8 | 2 | 28 | |
| 31 | 13 | 6 | | 0.5 | 15 | 15 | 5.5 | 5 | 15 | | | 25 |
| 32 | 5 | 12.5 | 14 | 0.5 | 20 | 15 | 2 | 7 | 8 | 2 | | 14 |
| 33* | 5 | 12.5 | 28 | 0.5 | 15 | 15 | | 9 | | | | |
| 34* | 5 | 12.5 | 29 | 0.5 | 10 | 15 | | 8 | | | | |

TABLE 6-continued

Additional Formulation Examples Demonstrating the Utility of the Invention

| Example | Terpene Resin | Pregelatinized Starch | Probe Tack g tack force | Tensile Strength g/cm^2 | 24 Hr Saline Absorption g/sq · m/24 hr |
|---|---|---|---|---|---|
| 26 | | | 504 | 1714 | 4788 |
| 27 | | | 757 | 1706 | 2688 |
| 28 | | | 467 | — | 6006 |
| 29 | | | 370 | 4778 | — |
| 30 | | | 644 | 975 | 6669 |
| 31 | | | 470 | 1318 | 3845 |
| 32 | | | 409 | 1673 | 1985 |
| 33* | | 15 | 456 | 1849 | 2772 |
| 34* | | 20 | 525 | 2076 | 2790 |

*Data for examples 33 and 34 is for extruded product.

What is claimed is:

1. A pressure sensitive hydrocolloid adhesive for medical use comprising the following composition by percentage weight:
   a) from about 2% to about 10% ethylene propylene rubber
   b) from about 9.5% to about 16% styrenic block copolymer
   c) from about 24% to about 33% tackifying resin
   d) from 0 to about 0.5% anti-oxidant
   e) from about 15% to about 35% NaCMC (Low DS)
   f) from about 5% to about 20% pectin
   g) from 0% to about 6% tackifier with softening point below about 37° C. comprising polyvinylcyclohexane
   h) from about 3% to about 12% plasticizer
   i) from 0% to about 25% NaCMC (high DS)
   j) from 0% to about 6% powdered cellulose
wherein the probe tack force in grams is in the range of 400–750, saline absorbency is in the range of about 500–5000 g/m$^2$/d, and tensile strength is in the range of about 500–3500 g/cm$^2$.

2. The hydrocolloid adhesive of claim 1 wherein the ethylene propylene rubber has a broad molecular weight distribution of lower molecular weight species and higher molecular weight species.

3. The hydrocolloid adhesive of claim 1 wherein the ethylene propylene rubber is amorphous and random.

4. The hydrocolloid adhesive of claim 1 wherein the ethylene propylene rubber has an ethylene content of 50% or less.

5. The hydrocolloid adhesive of claim 1 wherein the probe tack force in grams is in the range of 500–650 grams.

6. The hydrocolloid adhesive of claim 1 wherein the saline absorbency in grams per square meter for a 24 hour period is in the range of 1250–5000.

7. The hydrocolloid adhesive of claim 1 wherein the saline absorbency in grams per square meter for a 24 hour period is in the range of 2000–3500 when extruded.

8. The hydrocolloid adhesive of claim 1 wherein the saline absorbency in grams per square meter for a 24 hour period is in the range of 1500–2500 when non-extruded.

9. The hydrocolloid adhesive of claim 1 wherein the non-extruded tensile strength in grams per square centimeter is in the range of 800–1500.

10. The hydrocolloid adhesive of claim 1 wherein the tensile strength in grams per square centimeter is in the range of 500–3500.

11. The hydrocolloid adhesive composition of claim 1 wherein the extruded tensile strength is in the range of 1500–2500 grams per square centimeter.

12. The hydrocolloid adhesive of claim 1 wherein the probe tack is between about 300 to about 750 grams, force.

13. The hydrocolloid adhesive of claim 1 wherein the absorption of saline at 37° C. is between about 500 and about 5,000 grams per square meter per day.

14. The hydrocolloid adhesive of claim 1 wherein the tensile strength is between about 500 and 3,500 grams per square centimeter.

15. The hydrocolloid adhesive of claim 1 wherein the tackifier softening point is below about 37° C.

16. A pressure sensitive hydrocolloid adhesive for medical use comprising the following composition by percentage weight:
   a) from about 2% to about 20% ethylene propylene rubber
   b) from about 2% to about 16% styrenic block copolymer
   c) from about 14% to about 33% tackifying resin
   d) from 0% to about 0.5% anti-oxidant
   e) from about 10% to about 35% NaCMC with degree of substitution below 1.0
   f) from 0% to about 30.5% pectin
   g) from about 3% to about 12% plasticizer
   h) from 0% to about 6% tackifier with softening point below about 37° C. comprising polyvinylcyclohexane
   i) from 0% to about 25% NaCMC with degree of substitution above 1.0
   j) from 0% to about 6% powdered cellulose
wherein the probe tack force in grams is in the range of 400–750, saline absorbency is in the range of about 500–5000 g/m$^2$/d, and tensile strength is in the range of about 500–3500 g/cm$^2$.

17. The hydrocolloid adhesive of claim 16 wherein the probe tack is between about 300 to about 750 grams, force.

18. The hydrocolloid adhesive of claim 16 wherein the absorption of saline at 37° C. is between about 500 and about 5,000 grams per square meter per day.

19. The hydrocolloid adhesive of claim 16 wherein the tensile strength is between about 500 and 3,500 grams per square centimeter.

20. A pressure sensitive hydrocolloid adhesive for medical use comprising the following composition by percentage weight:
   a) from about 11.5% to about 36% of a hydrocolloid blend of ethylene propylene rubber and styrenic block copolymer
   b) from about 24% to about 39% tackifying resin
   c) from 0% to about 0.5% anti-oxidant
   d) from about 20% to about 52% absorbent powder selected from the group consisting of NaCMC pectin, powdered cellulose, pregelatinized starch, powdered fillers, fibers, absorbents, and super absorbents e) from about 3% to about 12% plasticizer f) from 0% to about 6% tackifier with softening point below about 37° C. comprising polyvinylcyclohexane g) from 0% to about 25% NaCMC with degree of substitution above 1.0 h) from 0% to about 6% powdered cellulose wherein the probe tack force in grams is in the range of 400–750, saline absorbency is in the range of about 500–5000 g/m$^2$/d, and tensile strength is in the range of about 500–3500 g/cm$^2$.

21. The hydrocolloid adhesive of claim 20 wherein the probe tack is between about 300 to about 750 grams, force.

22. The hydrocolloid adhesive of claim 20 wherein the absorption of saline at 37° C. is between about 500 and about 5,000 grams per square meter per day.

23. The hydrocolloid adhesive of claim 20 wherein the tensile strength is between about 500 and 3,500 grams per square centimeter.

* * * * *